United States Patent [19]

Stahly et al.

[11] Patent Number: 5,136,115
[45] Date of Patent: Aug. 4, 1992

[54] BROMOALKYLATION OF AROMATIC COMPOUNDS

[76] Inventors: Barbara C. Stahly, 517 Corsair Dr.; Brigitte Benage, 10242 Winterhue, both of Baton Rouge, La. 70810

[21] Appl. No.: 468,138

[22] Filed: Jan. 22, 1990

Related U.S. Application Data

[63] Continuation-in-part of Ser. No. 270,621, Nov. 14, 1988, abandoned.

[51] Int. Cl.⁵ .............................................. C07C 17/00
[52] U.S. Cl. .................................................. 570/195
[58] Field of Search ......................................... 570/195

[56] References Cited

U.S. PATENT DOCUMENTS

| | | | |
|---|---|---|---|
| 2,516,971 | 8/1950 | Galitzenstein | 570/195 |
| 2,714,125 | 7/1955 | Gerner | 570/195 |
| 3,311,602 | 3/1967 | Raley | 570/195 |
| 3,422,160 | 1/1969 | Napier | 570/195 |
| 4,536,595 | 8/1985 | Gradano | 562/406 |

FOREIGN PATENT DOCUMENTS

| | | | |
|---|---|---|---|
| 1135268 | 1/1982 | Canada | 570/195 |
| 1197254 | 11/1985 | Canada | |
| 47-39050 | 12/1972 | Japan | |
| 52-111536 | 9/1977 | Japan | |
| 1560082 | 1/1980 | United Kingdom | |

OTHER PUBLICATIONS

Mar., "Advanced Organic Chemistry," 2nd Ed. pp. 501–502 (1977).
Olah, "Friedel–Crafts and Related Reactions," vol. 2, pp. 659–784 (1964).
Palecek, (Zpch. Cert., of Authorship, pp. 219,752 (1982).

Primary Examiner—Michael L. Shippen
Attorney, Agent, or Firm—Richard J. Hammond

[57] ABSTRACT

The co-formation of diarylalkane by-product in the bromoalkylation of an aromatic compound with an ether corresponding to the formula R—O—R', wherein R is an α-chloroalkyl group containing at least two carbons and R' is R or alkyl, is minimized by conducting the reaction with agitation in the absence of a cosolvent and in the presence of both hydrogen sulfate and hydrogen bromide.

16 Claims, No Drawings

BROMOALKYLATION OF AROMATIC COMPOUNDS

CROSS REFERENCE TO RELATED APPLICATION

This application is a continuation-in-part of copending application Ser. No. 270,621, filed Nov. 14, 1988, now abandoned.

FIELD OF INVENTION

This invention relates to a process for bromoalkylating aromatic compounds to form 1-bromo-1-arylalkanes.

BACKGROUND

As disclosed in March, *Advanced Organic Chemistry*, Second Edition, McGraw-Hill, New York, 1977, pp. 501-502; Olah, *Friedel-Crafts and Related Reactions*, Volume 2, Interscience Publishers, New York, 1963-1964, pp. 659-784; U.S. Pat. No. 2,516,971 (Galitzenstein et al.); Canadian Patent 1,135,268 (Harris); and the references cited therein, it is known that aromatic compounds can be haloalkylated by reacting them with a hydrogen halide and an appropriate aldehyde, or with an α-haloalkyl ether or an α-haloalkyl alkyl ether, in the presence of a Lewis acid or a proton acid as a catalyst, most commonly in the presence of zinc chloride.

The haloalkylations utilizing formaldehyde or a formaldehyde-derived ether have been successfully employed in providing fairly high yields of 1-halo-1-arylalkanes, and reasonably high yields of 1-halo-1-arylalkanes have sometimes also been obtained from haloalkylations utilizing higher aldehydes or ethers derived from them. However, it has frequently not been found possible to provide commercially acceptable yields of 1-halo-1-arylalkane from the higher aldehydes and ethers, especially when the aromatic compound has been one of the less reactive ones, such as a monoalkylaromatic hydrocarbon. There has been too much co-formation of diarylalkane by-product.

It would be desirable to find a way of increasing the 1-halo-1-arylalkane yields obtainable from such processes to provide a more economical method of preparing, e.g., the 1-halo-1-(4-alkylphenyl)alkanes used in known processes, such as those of U.S. Pat. No. 4,536,595 (Gardano et al.), Canadian Patent 1,197,254 (Francalanci et al.), British Patent 1,560,082 (Dynamit Nobel), Czechoslovakian Certificate of Authorship 219,752 (Palecek et al.), and Japanese Kokai 47-39050 (Miyatake et al.) and 52-111536 (Tokutake).

Copending application Ser. No. 295,017 (Knesel), filed Aug. 17, 1989, discloses methods of improving the ratio of 1-halo-1-arylalkane to diarylalkane; but Knesel's ratios are not acceptably high at a sufficient degree of conversion to provide the yields of 1-halo-1-arylalkane that are desired.

THE INVENTION

It has now been found that 1-bromo-1-arylalkanes can be prepared with minimum co-formation of diarylalkane by-product, even when the aromatic reactant is a monoalkylaromatic hydrocarbon, by reacting one molar proportion of an aromatic compound having at least one free ring position with at least one molar proportion of an ether corresponding to the formula R—O—R', wherein R is an α-chloroalkyl group containing at least two carbons and R' is R or alkyl, with agitation at a temperature in the range of about −35° C. to about 0° C. in the absence of a cosolvent and in the presence of at least one molar proportion of hydrogen bromide and about 2-15 molar proportions of hydrogen sulfate.

The aromatic compound employed in the practice of the invention may be a carbocyclic aromatic compound, e.g., an unsubstituted aromatic hydrocarbon, such as benzene, naphthalene, anthracene, phenanthrene, etc; a polyalkylaromatic hydrocarbon, such as xylene, pseudo-cumene, mesitylene, etc.; an aromatic hydrocarbon bearing a substituent such as halo, cyano, nitro, hydroxy, alkoxy, phenoxy, alkylthio, etc. (e.g., the 2-, 3-, and 4-chloronitrobenzenes, the 2-, 3-, and 4-fluoronitrobenzenes, 4-fluoronitrobiphenyl, 6-methoxynaphthalene, phenoxybenzene, etc ); or it may be a heterocyclic aromatic compound, such as a chlorocarbazole, 2-phenyl-1-isoindolinone, 6-fluoro-5-nitroquinoline, etc. However, because of the commercial interest in their haloalkylated products and the difficulty that has previously been encountered in preparing the desired 1-halo-1-arylalkanes from them, the preferred aromatic compounds are monoalkylaromatic hydrocarbons, such as 1-methylnaphthalene, 2-methylnaphthalene, 9-methylanthracene, 9-butylanthracene, 9-dodecylanthracene, and the various monoalkylbenzenes, e.g., the methyl-, ethyl-, propyl-, isobutyl-, sec-butyl-, t-butyl-, isopentyl-, t-pentyl-, and hexylbenzenes. The most preferred aromatic compounds are the monoalkylbenzenes wherein the alkyl group contains 1-5 carbons.

The ether which is reacted with the aromatic hydrocarbon is an ether corresponding to the formula R—O—R', wherein R is an α-chloroalkyl group containing at least two carbons, preferably 2-20 carbons, and most preferably 2-6 carbons, and R' is R or an alkyl group which preferably contains 1-20 carbons, most preferably 1-6 carbons.

Exemplary of the ethers which may be employed are α-chloroethyl ether [also known as chloroethyl ether, 1-chloroethyl ether, bis(1-chloroethyl) ether, or di(1-chloroethyl) ether], α-chloropropyl ether, α-chlorobutyl ether, α-chloropentyl ether, α-chlorohexyl ether, α-chlorodecyl ether, α-chlorododecyl ether, α-chloropentadecyl ether, α-chlorooctadecyl ether, α-chloroeicosyl ether, α-chloroethyl methyl ether, α-chloroethyl ethyl ether, α-chloroethyl propyl ether, α-chlorobutyl butyl ether, α-chloropentyl methyl ether, α-chlorohexyl hexyl ether, etc. The preferred ethers are the α-chloroalkyl ethers, such as α-chloroethyl ether.

When not already available, the ethers may be formed by conventional techniques of reacting hydrogen chloride with the appropriate aldehyde and, when a chloroalkyl alkyl ether is desired, also with the appropriate alcohol to form the desired ether and water. The water may or may not be removed from the reaction product before the ether is used in the bromoalkylation process, but it is generally preferred to remove any water that would cause the water content of the bromoalkylation reaction mixture to exceed about 15% by weight of the catalyst used.

The amount of ether employed in the bromoalkylation reaction may be as small as the stoichiometric amount, i.e., the amount which provides one R group per molecule of aromatic hydrocarbon. However, it is generally preferred to employ an amount that provides at least two R groups per molecule of aromatic compound. There does not appear to be any maximum to the amount of ether that may be used other than the maximum that economics permit.

As in known processes, the bromoalkylation is conducted in the presence of an acid catalyst, preferably hydrogen sulfate. In order to avoid the presence of too much water in the reaction mixture, as well as to take advantage of commercially-available materials, the hydrogen sulfate is generally introduced in the form of 88-98% sulfuric acid. The amount employed is generally such as to provide at least about one mol, preferably at least about 2-6 mols, per mol of aromatic compound; and it ordinarily should not exceed about 15 mols per mol of aromatic compound.

The amount of hydrogen bromide used in the reaction is usually at least about one equivalent, based on the amount of aromatic compound; and it is generally introduced by bubbling it through the reaction mixture or by pressurizing the reaction vessel with it.

Since improved yields of 1-bromo-1-arylalkane are not obtained without it, the use of the hydrogen bromide is critical —a surprising factor, since the reaction mixture already contains an acid catalyst. It would therefore have been thought that additional acidity would not be necessary.

The reaction is usually conducted at a bath temperature in the range of about $-35°$ C. to about $0°$ C., preferably about $-20°$ C. to about $-10°$ C., in order to achieve the maximum advantages of the invention. The higher temperatures generally favor higher conversions, while the lower temperatures are apt to favor higher bromoalkylation product/diarylalkane ratios.

As already mentioned, the reaction is conducted in the absence of a cosolvent, i.e., an organic material other than a reactant which could serve to solvate the ingredients of the reaction mixture.

The manner of combining the ingredients does not appear to be critical. For example, (1) the ether, which may be a pure ether or a crude ether contaminated with water and/or hydrogen chloride, may be dissolved in the aromatic compound and added to the catalyst while bubbling hydrogen bromide through the reaction mixture, (2) the catalyst may be added to such a pure or crude ether prior to the addition of the aromatic compound, (3) the pure or crude ether, the aromatic compound, and the catalyst may be combined in either fashion in a reaction vessel which is pressurized with the hydrogen bromide, etc.

The invention is useful as an alternative method of preparing 1-bromo-1-arylalkanes from aromatic compounds that are known to be capable of providing high yields of such products by known bromoalkylation techniques. However, it is particularly advantageous as a method of preparing 1-bromo-1-arylalkanes from the less reactive aromatic hydrocarbons, such as monoalkylbenzenes, that have not previously been found to be capable of providing high yields of such products by bromoalkylation processes other than bromomethylations.

As is known, the products obtained by the process are useful as internal standards, intermediates for the preparation of monomers, detergents, pharmaceuticals, etc. When they are used as chemical intermediates, they may be subjected to the same reactions as have previously been used to convert them to desired products. For example, the 1-bromo-1-phenylethanes can be dehydrohalogenated in any known manner to provide styrenes which can then be polymerized by known techniques.

A particularly interesting application of the 1-bromo-1-(4-alkylphenyl)ethanes which are prepared in a preferred embodiment of the invention is as intermediates for the preparation of ibuprofen and related pharmaceuticals. When they are used in such applications, they may be converted to the desired products in any suitable manner. For example, they may be reacted with carbon monoxide in the presence of a carbonylation catalyst and then acidified to the corresponding propionic acids as in Gardano et al., Francalanci et al., or Dynamit Nobel; or they may be cyanated and then acidified to the corresponding propionic acids as in Palecek et al. or Tokutake. Another useful synthesis involves reacting the compounds with magnesium, carbonating the resultant Grignard reagent with carbon dioxide, and acidifying the carbonated product to the propionic acid as in Miyatake et al.

It is obvious that many variations may be made in the products and processes set forth above without departing from the spirit and scope of this invention.

What is claimed is:

1. A process which comprises reacting one molar proportion of an aromatic compound having at least one free ring position with at least one molar proportion of an ether corresponding to the formula R—O—R', wherein R is an α-chloroalkyl group containing at least two carbons and R' is R or alkyl, with agitation at a temperature in the range of about $-35°$ C. to about $0°$ C. in the absence of a cosolvent and in the presence of at least one molar proportion of hydrogen bromide and about 2-15 molar proportions of hydrogen sulfate to bromoalkylate the aromatic compound while minimizing the co-formation of diarylalkane by-product.

2. The process of claim 1 wherein the aromatic compound is a monoalkylbenzene.

3. The process of claim 2 wherein the monoalkylbenzene is one in which the alkyl substituent contains 1-5 carbons.

4. The process of claim 3 wherein the monoalkylbenzene is isobutylbenzene.

5. The process of claim 1 wherein the ether is one in which R is an α-chloroalkyl group containing 2-20 carbons and R' is R or an alkyl group containing 1-20 carbons.

6. The process of claim 5 wherein the ether is one in which R is an α-chloroalkyl group containing 2-6 carbons and R' is R or an alkyl group containing 1-6 carbons.

7. The process of claim 6 wherein the ether is an α-chloroalkyl ether.

8. The process of claim 7 wherein the α-chloroalkyl ether is α-chloroethyl ether.

9. The process of claim 1 wherein the amount of ether employed is such as to provide at least two R groups per molecule of aromatic compound.

10. The process of claim 1 wherein the reaction temperature is in the range of about $-20°$ C. to about $-10°$ C..

11. The process of claim 1 wherein the amount of hydrogen sulfate is about 2-6 mols per mol of aromatic compound.

12. The process of claim 1 wherein the hydrogen sulfate is introduced into the reaction mixture in the form of 88-98% sulfuric acid.

13. The process of claim 1 wherein the reaction is conducted in the absence of more than about 15% by weight of water, based on the weight of the hydrogen sulfate.

14. The process of claim 1 wherein the hydrogen bromide is introduced by bubbling it through the reaction mixture.

15. The process of claim 1 wherein the hydrogen bromide is introduced by pressurizing the reaction vessel with it.

16. The process of claim 1 wherein one molar proportion of isobutylbenzene is bromoethylated by reacting it with at least about two molar proportions of α-chloroethyl ether at a temperature in the range of about −20° C. to about −10° C. in the presence of about 2–6 molar proportions of hydrogen sulfate and in the absence of a cosolvent or more than about 15% by weight of water, based on the weight of the hydrogen sulfate, while bubbling hydrogen bromide through the reaction mixture or pressurizing the reaction vessel with hydrogen bromide; the hydrogen sulfate being introduced in the form of 88–98% sulfuric acid.

* * * * *